United States Patent
Neiss et al.

(10) Patent No.: US 7,679,740 B2
(45) Date of Patent: Mar. 16, 2010

(54) METHOD AND APPARATUS FOR MULTIMODAL DETECTION

(75) Inventors: Jason Neiss, Pittsburgh, PA (US); Robert Schweitzer, Pittsburgh, PA (US); Patrick J. Treado, Pittsburgh, PA (US)

(73) Assignee: ChemImage Corporation, Pittsburgh, PA (US)

( * ) Notice: Subject to any disclaimer, the term of this patent is extended or adjusted under 35 U.S.C. 154(b) by 35 days.

(21) Appl. No.: 11/632,471

(22) PCT Filed: Jul. 14, 2005

(86) PCT No.: PCT/US2005/025112
§ 371 (c)(1),
(2), (4) Date: Jan. 16, 2007

(87) PCT Pub. No.: WO2006/019991
PCT Pub. Date: Feb. 23, 2006

(65) Prior Publication Data
US 2008/0084553 A1    Apr. 10, 2008

Related U.S. Application Data

(60) Provisional application No. 60/588,212, filed on Jul. 15, 2004.

(51) Int. Cl.
*G01J 3/44* (2006.01)
(52) U.S. Cl. ........................................ 356/301
(58) Field of Classification Search ............... 356/301; 702/22
See application file for complete search history.

(56) References Cited

U.S. PATENT DOCUMENTS

| | | | | |
|---|---|---|---|---|
| 5,606,164 A * | 2/1997 | Price et al. | ............. | 250/339.09 |
| 6,075,891 A * | 6/2000 | Burman | ............. | 382/191 |
| 6,421,553 B1 * | 7/2002 | Costa et al. | ............. | 600/476 |
| 2004/0051867 A1 * | 3/2004 | Brestel et al. | ............. | 356/318 |
| 2005/0137806 A1 * | 6/2005 | Kutsyy et al. | ............. | 702/19 |
| 2006/0100524 A1 * | 5/2006 | Lucassen et al. | ............. | 600/476 |

OTHER PUBLICATIONS

Rosch et al, Chemotaxonomic Identification of Single Bacteria by Micro-Raman Spectroscopy: Application to Clean-Room-Relevant Biological Contaminations, Applied and Environmental Microbiology, Mar. 2005, p. 1626-1637.*

* cited by examiner

*Primary Examiner*—Tarifur Chowdhury
*Assistant Examiner*—Jonathon D Cook
(74) *Attorney, Agent, or Firm*—Duane Morris LLP (57) ABSTRACT

Methods for detecting and classifying an unknown substance in a sample include the steps of (a) providing a spectrum for each of a predetermined number of reference substances; (b) detecting an area of interest that contains the unknown substance; (c) targeting the area of interest; (d) determining a spectrum of the unknown substance from the area of interest; (e) comparing the determined spectrum of the unknown substance with the spectrum of one or more of the reference substances; and (f) classifying the unknown substance based on the comparison of spectra. Systems for performing these methods include means for providing a spectrum for a predetermined number of reference substances, means for detecting an area of interest on a sample that contains an unknown substance to be classified, means for targeting this area of interest, means for determining a spectrum of the unknown substance in the area of interest, means for comparing this spectrum with the spectrum of one or more of the reference substances, and means for classifying the unknown substance based on the comparison of spectra.

28 Claims, 7 Drawing Sheets

ND APPARATUS FOR
MULTIMODAL DETECTION

The instant disclosure claims filing-date priority to the Provisional Application No. 60/588,212 filed Jul. 15, 2004, the specification of which is incorporated herein in its entirety.

BACKGROUND

It is becoming increasingly important and urgent to rapidly and accurately identify toxic materials or pathogens with a high degree of reliability, particularly when the toxins/pathogens may be purposefully or inadvertently mixed with other materials. In uncontrolled environments, such as the atmosphere, a wide variety of airborne organic particles from humans, plants and animals occur naturally. Many of these naturally occurring organic particles appear similar to some toxins and pathogens even at a genetic level. It is important to be able to distinguish between these organic particles and the toxins/pathogens.

In cases where toxins and/or pathogens are purposely used to inflict harm or damage, they are typically mixed with so-called "masking agents" to conceal their identity. These masking agents are used to trick various detection methods and apparatus to overlook or be unable to distinguish the toxins/pathogens mixed therewith. This is a recurring concern for homeland security where the malicious use of toxins and/or infectious pathogens may disrupt the nation's air, water and/or food supplies. Additionally, certain businesses and industries could also benefit from the rapid and accurate identification of the components of mixtures and materials. One such industry that comes to mind is the drug manufacturing industry, where the identification of mixture composition could aid in preventing the alteration of prescription and non-prescription drugs.

One known method for identifying materials and organic substances contained within a mixture is to measure the absorbance, transmission, reflectance or emission of each component of the given mixture as a function of the wavelength or frequency of the illuminating or scattered light transmitted through the mixture. This, of course, requires that the mixture be separable into its component parts. Such measurements as a function of wavelength or frequency produce a signal that is generally referred to as a spectrum. The spectra of the components of a given mixture, material or object, i.e., a sample spectra, can be identified by comparing the sample spectra to set a reference spectra that have been individually collected for a set of known elements or materials. The set of reference spectra are typically referred to as a spectral library, and the process of comparing the sample spectra to the spectral library is generally termed a spectral library search. Spectral library searches have been described in the literature for many years, and are widely used today. Spectral library searches using infrared (approximately 750 nm to 100 μm wavelength), Raman, fluorescence or near infrared (approximately 750 nm to 2500 nm wavelength) transmissions are well suited to identify many materials due to the rich set of detailed features these spectroscopy techniques generally produce. The above-identified spectroscopic techniques produce rich fingerprints of the various pure entities, which can be used to identify the component materials of mixtures via spectral library searching.

Conventional library searches generally cannot even determine the composition of mixtures—they may be used if the user has a pure target spectrum (of a pure unknown) and would like to search against the library to identify the unknown compound. Further, library searches have been found to be inefficient and often inaccurate. Where time is of the essence searching a component library can be exceedingly time consuming and if the sample under study is not a pure component, a search of pure component library will be futile.

SUMMARY

In one embodiment, the disclosure relates to a method for detecting and classifying an unknown substance comprising the steps of (a) providing a spectrum for each of a predetermined number of reference substances; (b) detecting an area of interest on said unknown substance; (c) targeting said area of interest; (d) determining a spectrum from said area of interest; (e) comparing the determined spectrum with the spectrum of one of the reference substances; and (f) classifying said unknown substance based on the comparison of spectra.

In another embodiment, the disclosure relates to a method for detecting and classifying an unknown substance comprising (a) providing a spectrum for each of a predetermined number of reference substances and determining therefrom a first set of eigenvectors using principal components analysis ("PCA") to thereby determine a first set of reduced reference models; (b) detecting an area of interest on said unknown substance; (c) targeting said area of interest; (d) determining a spectrum from said area of interest and determining therefrom a reduced test spectrum as a function of said first set of eigenvectors; (e) comparing the reference models with the reduced test spectrum; and (f) classifying said unknown substance based on said comparison of reduced spectra.

In another embodiment, the disclosure relates to a system for detecting and classifying an unknown substance comprising: (a) means for providing a spectrum for each of a predetermined number of reference substances; (b) means for detecting an area of interest on said unknown substance; (c) means for targeting said area of interest; (d) means for determining a spectrum from said area of interest; (e) means for comparing the determined spectrum with the spectrum of one of the reference substances; and (f) means for classifying said unknown substance based on the comparison of spectra.

In still another embodiment, the disclosure relates to A system for detecting and classifying an unknown substance comprising (a) means for providing a spectrum for each of a predetermined number of reference substances and determining therefrom a first set of eigenvectors using principal components analysis ("PCA") to define a first set of reduced reference models; (b) means for detecting an area of interest on said unknown substance; (c) means for targeting said area of interest; (d) means for determining a spectrum from said area of interest and determining therefrom a reduced spectrum as a function of said first set of eigenvectors; (e) means for comparing the reference models with the second reduced spectrum; and (f) means for classifying said unknown substance based on said comparison of reduced spectra.

DETAILED DESCRIPTION

The instant disclosure relates to a method and apparatus for implementing multi-modal detection. More specifically, the disclosure relates to a method and apparatus configured to examine and identify an unknown substance. The unknown substance may include a chemical substance, a biological material or a combination of the chemical and biological material. The unknown substance may also contain a combination of toxic, hazardous and inert material in a physical mixture.

An apparatus according to one embodiment of the disclosure includes one or more detection probes or sensors in communication with an illumination source and a controller mechanism. The sensors can be devised to receive spectral and other attributes of the sample and communicate said information to the controller. The controller may include one or more processors in communication with a database for storing spectral library or other pertinent information for known samples. The processor can be programmed with various detection algorithms defining instructions for identification of the unknown sample.

Figure 1:
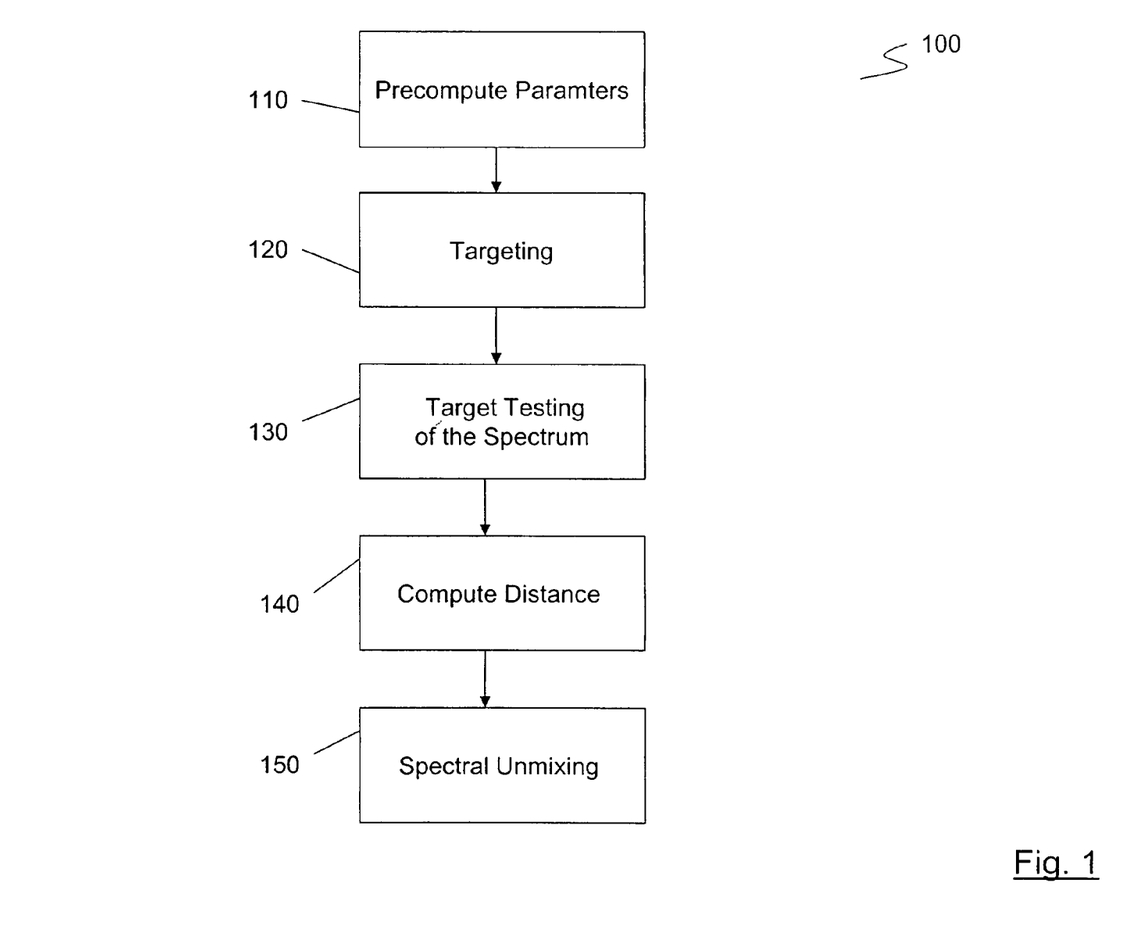
FIG. 1 is an exemplary detection diagram according to one embodiment of the disclosure.

FIG. 1 is an exemplary detection algorithm according to one embodiment of the disclosure. Flow diagram 100 defines an algorithm for implementing a series of instructions on a processor. In step 110, the detection algorithm 100 defines pre-computation parameters stored in a library. In any detection or classification application, the more a priori information available about the desired targets and undesired backgrounds and interference, the better the expected detection probability. The pre-computation parameters may include assembling a library of known samples. The library may include, for example, a spectral library or a training set. In one embodiment, the library includes entire optical, UV and Raman images of known substances and biological material. If the algorithm is configured for a multimodal device, step 110 may also include defining additional parameters such as shape, size, color or the application of a pattern recognition software. If one of the contemplated modes is UV fluorescence, then step 110 may include storing fluorescence spectra directed to identifying the UV signature of known substances including biological substances. If one of the contemplated modes is Raman imaging, then step 110 may further include storing Raman parameters (i.e., spectra) of various known substances.

To address this issue, in one embodiment the disclosure relates to reducing complex datasets to a more manageable dataset by instituting principal component analysis ("PCA") techniques. The PCA analysis allows storing the most pertinent (alternatively, a reduced number of data points) in the library. Stated differently, PCA can be used to extract features of the data that may contribute most to variability. By storing PCA eigenvectors tractable storage of class variability can substantially reduce the volume of stored data in the library. While the PCA eigenvectors are not identifiers per se, they allow tractable storage of class variability. They are also a key component of subspace-based detectors. Moreover, the information in the library is dependent on the type of classifier used. A classifier, can be any arbitrary parameter that defines one or more attribute of the stored data. For example, the Mahalanobis classifier requires the average reduced spectrum and covariance matrix for each type of material, or class, in the library. In one embodiment, a class can be an a priori assignment of a type of known material. For example, using an independently validated sample of material, one can acquire spectral data and identify the data as belonging to material from that sample. Taking multiple spectra from multiple samples from such a source, one can create a class of data for the classification problem.

As stated, the multimodal library can store training data. The training algorithm typically includes pure component material data and instructions for extracting applicable features therefrom. The applicable features may include: optical imaging, morphological features (i.e., shape, color, diameter, area, perimeter), UV fluorescence (including full spectral signatures), Raman dispersive spectroscopy and Raman imaging (including full spectral signatures). Using PCA techniques in conjunction with the training algorithm, the data can be reduced to eigenvectors to describe the variability inherent within the material and represent reduced dimensional subspaces for later detection and identification.

Thus, according to one embodiment, step 110 includes: (a) defining the overall PCA space; (b) defining the so-called confusion areas; (c) defining classes and subclasses in the same PCA space (compute model parameters); (d) defining sub-spectral bands (e.g., CH-bands and other common fingerprints); (e) computing threat morphological features.

Once a sample is selected for testing, the first step is to narrow the field of view ("FOV") of the detection probe to the sub-regions of the sample containing the most pertinent information. The sub-regions may include portions of the sample containing toxic chemical or adverse biological material. To this end, step 120 of FIG. 1 is labeled targeting. In bio-threat identification applications time is of the essence. The FOV and the time to identify are related to the spectral signal to noise ratio ("SNR") achievable. Higher SNR can be obtained from interrogating regions containing high amounts of suspect materials, so total acquisition time is reduced by carefully determining specific interrogation regions.

In one embodiment, the disclosure relates to identifying those candidate regions using rapid sensors. The FOV selection of specific candidate regions defines targeting. In one embodiment, targeting is reduced to a multi-tiered approach whereby each tier eliminates objects that do not exhibit properties of the target. For example, targeting may include optical imaging and UV fluorescence imaging. In optical imaging, the sample is inspected for identifying target substances having particular morphology features. In UV fluorescence imaging, the target may be a biological material that fluoresces once illuminated with the appropriate radiation source. If multiple sensors are used, each sensor can be configured for a specific detection. If on the other hand, a multi-mode single sensor is used, each sensor modality can have characteristics that lend itself to either targeting or identification. Table 1 shows exemplary sensors characteristics.

TABLE 1

Sensor Characteristics

| Sensor | Sensitivity | Specificity | Acquisition Time | Purpose |
|---|---|---|---|---|
| Optical Imaging | High | Low | Low | Targeting |
| UV Fluorescence imaging | High | Medium | Low-Medium | Targeting |
| Raman Dispersive | Low | Very High | Low | Identification |
| Raman Imaging | Low | Very High | High | Identification |

The optical imaging mode can recognize potential threat material via morphological features while UV Fluorescence imaging is sensitive to biological material. Combining the results of the two modes can result in identifying locations containing biological material that exhibits morphological properties of bio-threat or hazardous agents.

In step 130 of FIG. 1, the algorithm calls for targeting the sample. In this step the FOV is narrowed to one ore more target regions and each region is examined to identify its composition. In one embodiment, the testing step may include Raman acquisition. The Raman acquisition algorithm can be configured to operate with minimal operator input. Eventual bio-threat detection systems can be fully automated to ensure that the test spectrum is suitable for the detection process. Because detection probability depends highly on the test spectrum's signal-to-noise ratio ("SNR"), the system can be programmed to ignore any spectra falling below a pre-defined threshold. In one exemplary embodiment, SNR of about 20 is required for accurate detection. The SNR determination can be based on examining the signal response in CH-regions as compared to a Raman-empty (i.e., noise-only) region. If the target spectrum readily matches that of a known substance, then the target identification task is complete and the system can generate a report. If on the other hand, the target spectrum is not defined by the pre-computed parameters, then it can be mapped into PCA space for dimension reduction and outlier detection (see step 140 in FIG. 1). Outlier detection involves determining if the spectrum is significantly different from all classes to indicate a possible poor acquisition or the presence of an unknown material.

Conventional detection and classification methods address the problem of identifying targets when background noise and other interferences are paramount. Such methods include, for example, linear discriminant analysis (LDA), adaptive matched filter classifiers (AMF), adaptive matched subspace detectors (AMSD) and orthogonal subspace (OSP) projection derived classifiers.

According to one embodiment of the disclosure a heuristic method is used to identify and to compare the dispersive test spectrum with each candidate class and choose the class closest to the test spectrum by measuring the minimum distance measured with a known metric. One such computational metric is derived from Euclidean geometry. The Euclidian distance (or minimum Euclidean distance) compares two vectors of length n by:

$$d_E = |x-y| = \left(\sum_{i=1}^{n} |x_i - y_i|^2\right)^{1/2} \quad (1)$$

In the stated embodiment, x and y are two full-length spectral vectors.

In accordance with one embodiment of the disclosure, the distance $d_E$ is calculated for the test spectrum against the average spectrum of each training classes along with each spectrum in a comprehensive spectral library comprised of a single spectrum per class (see step 110). If the minimum Euclidean distance ($d_E$) results in a unique match that is one of the full training classes, it may be reported as the identity of the sample. On the other hand, if the minimum Euclidean distance does not match one of the training classes, the Mahalanobis distance can be used next to further identify the sample. The Mahalanobis metric can be viewed as an extension of Euclidean distance which considers both the mean spectrum of a class and the shape, or dispersion of each class. The dispersion information is captured in the covariance matrix C and the distance value can be calculated as follows:

$$d_M = [(x-y)^T \cdot C^{-1} \cdot (x-y)]^{1/2} \quad (2)$$

An advantage of estimating the Mahalanobis distance, $d_M$, is that it accounts for correlation between different features and generates curved or elliptical boundaries between classes. In contrast, the Euclidean distance, $d_E$, only provides spherical boundaries that may not accurately describe the data-space. In equation (2), C is the covariance matrix that is defined for each class from the eigenvector PCA value. Thus, according to one embodiment of the disclosure, the training library defines a set of mean vectors and covariance matrices derived from the PCA eigenvectors of each class. In addition to checking for minimum distance, one embodiment the disclosure determines whether the test spectrum lies in the so-called confusion region of overlapping classes. The mean vector and covariance matrix define a hyper-ellipse with dimensions equal to the number of eigenvectors stored for each model. When projected onto two dimensions for visualization, ellipses can be drawn around the 2-σ confidence interval about the mean for each class. If the test spectrum (represented by a point in the principal component space (PC space) lies within the 2-σ interval (for each projection) it is likely a member of that class. Thus, the overlap regions can be clearly seen, and if a test spectrum is a member of more than one class, the spectrum is likely a mixture of more than one component. In one embodiment of the disclosure an imaging channel and a spectral unmixing algorithms are used to identify the contents of the mixture.

The specified spectral unmixing algorithm is capable of determining the constituents of a mixed spectrum and their level of purity or abundance. Thus, when a unique class is not determined from a dispersive spectrum through Mahalanobis distance calculation, spectral unmixing can be used. An exemplary unmixing algorithm is disclosed in PCT Application No. PCT/US2005/013036 filed Apr. 15, 2005 by the assignee of the instant application, the specification of which is incorporated herein in its entirety for background information.

If neither Raman imaging nor spectral unmixing is capable of identifying the sample's spectrum, or if the spectrum represents an outlier from the library classes, the decomposition method of Ramanomics can be implemented. Ramanomics defines a spectrum according to its biochemical composition. More specifically, Ramanomics determines whether the composition is composed of proteins, lipids or carbohydrates and the percent of each component in the composition. According to one embodiment, the constituent amounts are estimated by comparing the input spectrum to spectra from each of the constituents.

In step 150 a report is generated to identify the sample's composition. Depending on the analysis technique, different results can be reported. The results may include a unique class, a list of overlapping classes, a pure non-library class or the presence of an outlier component. If a unique class is identified, the results may include a corresponding confidence interval obtained based on Euclidean or Mahalanobis distance values.

Figure 2:
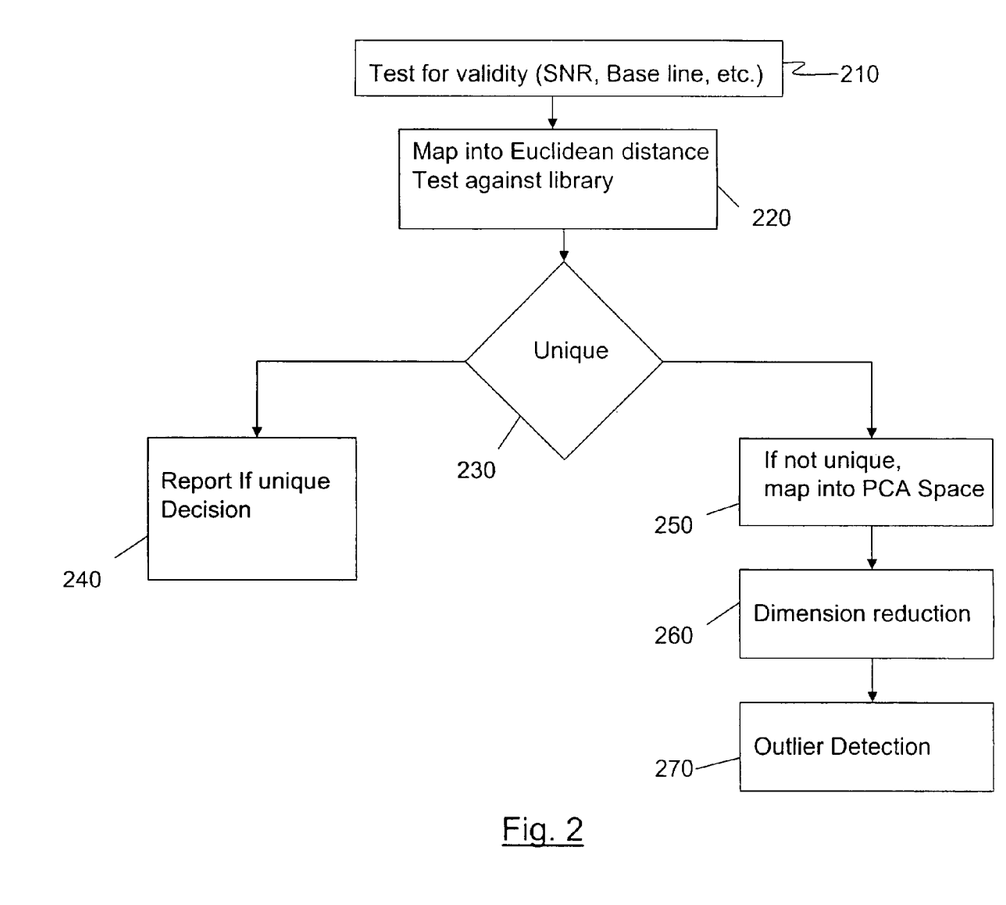
FIG. 2 provides an exemplary algorithm for targeting a region of interest likely to provide a quality test spectrum.

FIG. 2 provides an exemplary algorithm for target testing of the spectrum. In step 210 of FIG. 2 a test is conducted to assess validity of the spectrum. As stated, this can be accomplished by comparing the sample's spectrum against a pre-defined threshold or baseline. In step 220, the sample's spectra is mapped into the Euclidean space. This can be done, for example by determining $d_E$ according to equation (1). Once mapped into the Euclidean space, the distance can be tested against library classes not defined by pre-compute parameters (see step 110, FIG. 1). If the distance $d_E$ is not defined by the library of parameter, then the sample under test can represent a unique material. Should this be the case, the result can be reported as shown in step 240. If the $d_E$ does not represent a unique material (step 230) then its spectra can be mapped into PCA space (step 250) for dimension reduction (step 260) and for outlier detection (step 270). Dimension reduction can be accomplished through conventional PCA techniques.

If the sample is determined to be an outlier, then its spectra can be saved for review. Alternatively, Ramanomics can be used to further determine whether the sample is a mixture. If the sample is not a mixture then it can be identified as a new class of material.

Figure 3:
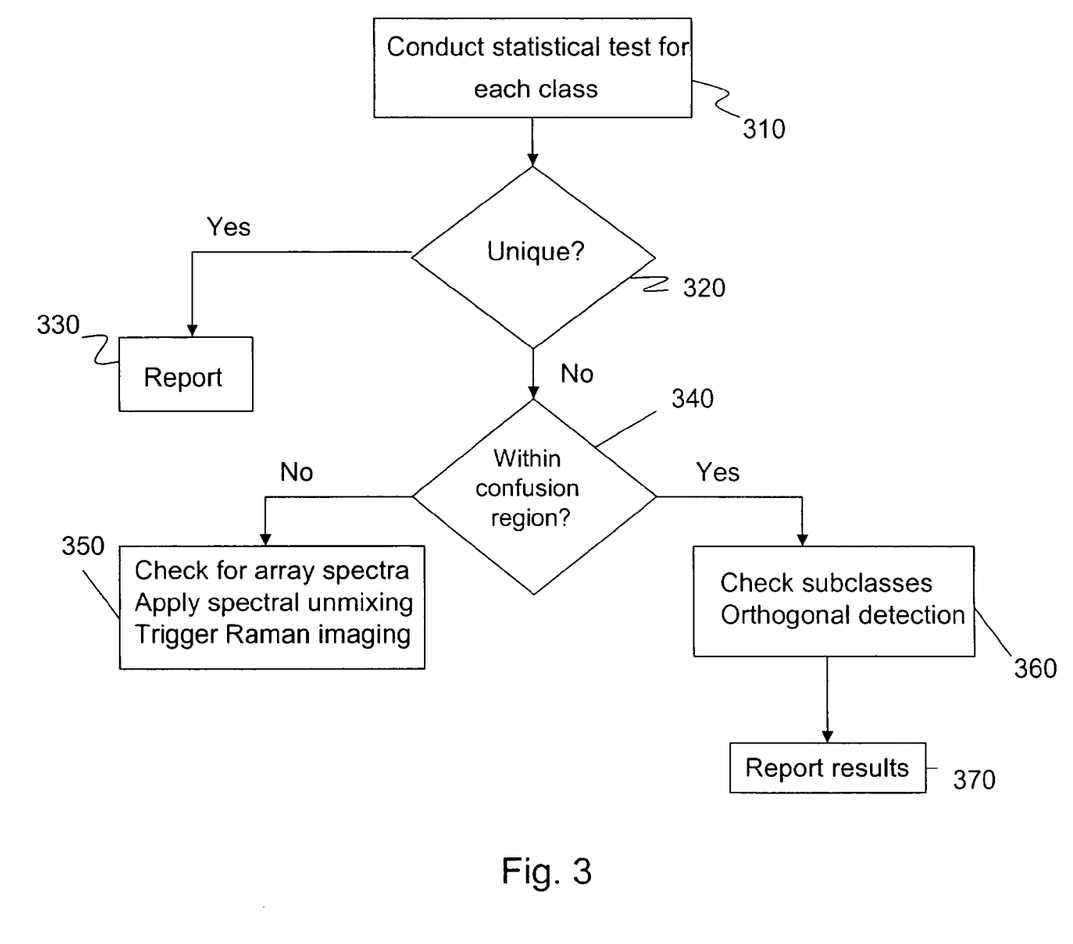
FIG. 3 is an exemplary algorithm for computing the distance represented by a sample from each known class in the library.

FIG. 3 is an exemplary algorithm for computing the distance represented by a sample from each known class in the library. In step 310 a statistical test is performed for each class of material identified within the sample. The statistical test may determine whether the material is a unique material (see step 320). If the material is unique, then it can be reported immediately according to step 320. If the statistical test shows that the material is not unique, then it must be determined whether the sample result is within the confusion region (step 340). The statistical test can be Euclidean Distance, Mahalanobis Distance, or other similar distance metrics. Subspace detection methods use hypothesis testing and generalized likelihood tests to assess similarity, If it is determined that the material is within the confusion region, the various subclasses, stored in the library, are assessed to determine whether the sample belongs to any such subclass. To this end, a method of orthogonal detection can be implemented to determine whether the sample matches any such subclass. According to one embodiment of the disclosure, the orthogonal detection consists of performing wide-field Raman imaging on the region to derive a spectral signature for each pixel in a spectral image. These spatially-localized spectra are then classified individually to produce a classified Raman image.

If the material is within a confusion region (step 350), then one or more of the following steps can be implemented: (1) check the fiber array spectra; (2) apply spectral unmixing; (3) conduct orthogonal detection and Raman imaging of the sample; and (4) save the results for review. In implementing the step of checking the fiber array spectra the dispersive Raman detector produces an average signal taken over a spatial FOV by combining signals from a set of optical fibers. By examining the individual fibers and their corresponding signals, one embodiment of the disclosure obtains more local spectral estimates from points within the FOV. These local spectra are more likely to be pure component estimates than the overall average dispersive spectrum.

The step of conducting Raman imaging can be implemented because dispersive spectroscopy integrates the Raman signal over an entire FOV. Thus, if more than one material occupies the FOV, the spectrum will be a mixture of all those components. One solution is to increase the spatial resolution of the sensor. According to this embodiment, a wide-field Raman imaging system is employed. If a suspected target arises from the dispersive analysis, Raman imaging can isolate the target component. In this manner, Mahalanobis distance test can be performed on each spectrum in the Raman image.

If the sample is determined to be outside of all classes (not shown in FIG. 3), then the algorithm can check the fiber array spectra (or nominal mixture spectra) to determine whether the sample defines a mixture. If so, a spectral unmixing algorithm can be implemented to determine its components and their amounts. Further orthogonal detection can also be implemented at this stage through Raman imaging to further the analysis. In step 370, the results are reported to the operator.

Figure 4:
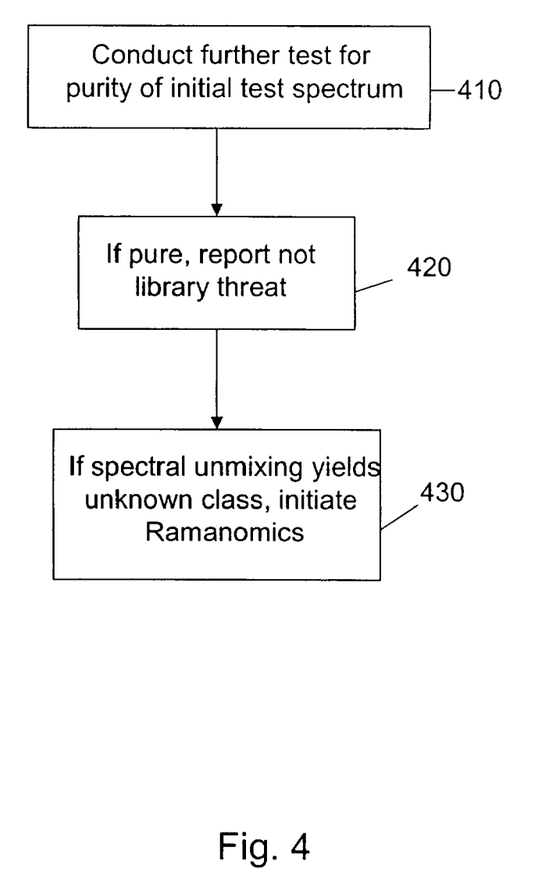
FIG. 4 is an exemplary algorithm for spectral unmixing.

In the event that the above algorithms are unable to determine the sample's composition, spectral unmixing can be implemented. FIG. 4 is an exemplary algorithm for spectral unmixing if Mahalanobis sequence fails to identify the sample's composition. Assuming that the spectral unmixing is unsuccessful, step 410 of FIG. 4 calls for further testing to determine the purity of the initial test spectrum. Purity assessment involves examining the intermediate results from spectral unmixing to assess the correlation of the spectrum with all the library entries and combinations of library entries.

If it is determined that the initial test spectrum defines a pure sample, then it will be reported that the material under study does not pose a threat and a Ramanomics algorithm is initiated. In addition, if the spectral unmixing yields unknown class, Ramanomics algorithm is also initiated to determine the relative similarity of the test spectrum to biological compounds.

Figure 5:
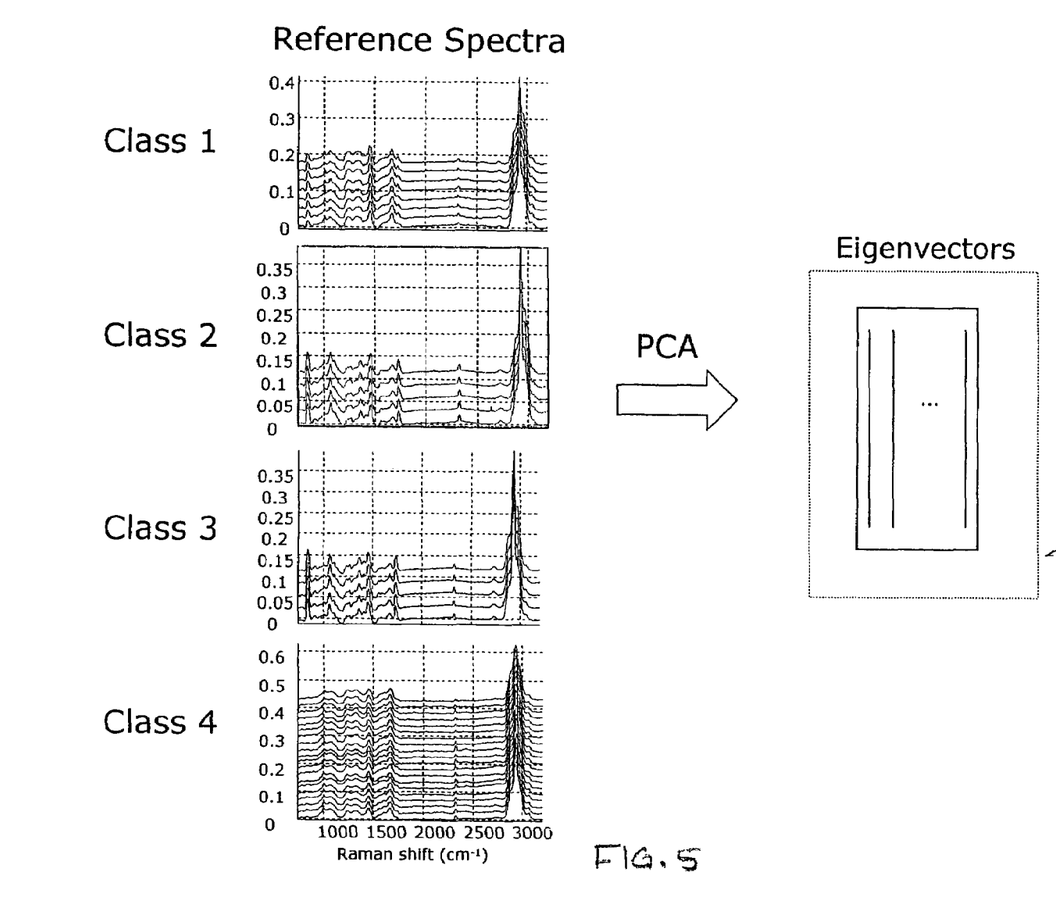
FIG. 5 shows a method for determining eigenvectors from reference spectra according to one embodiment of the disclosure.
Figure 6:
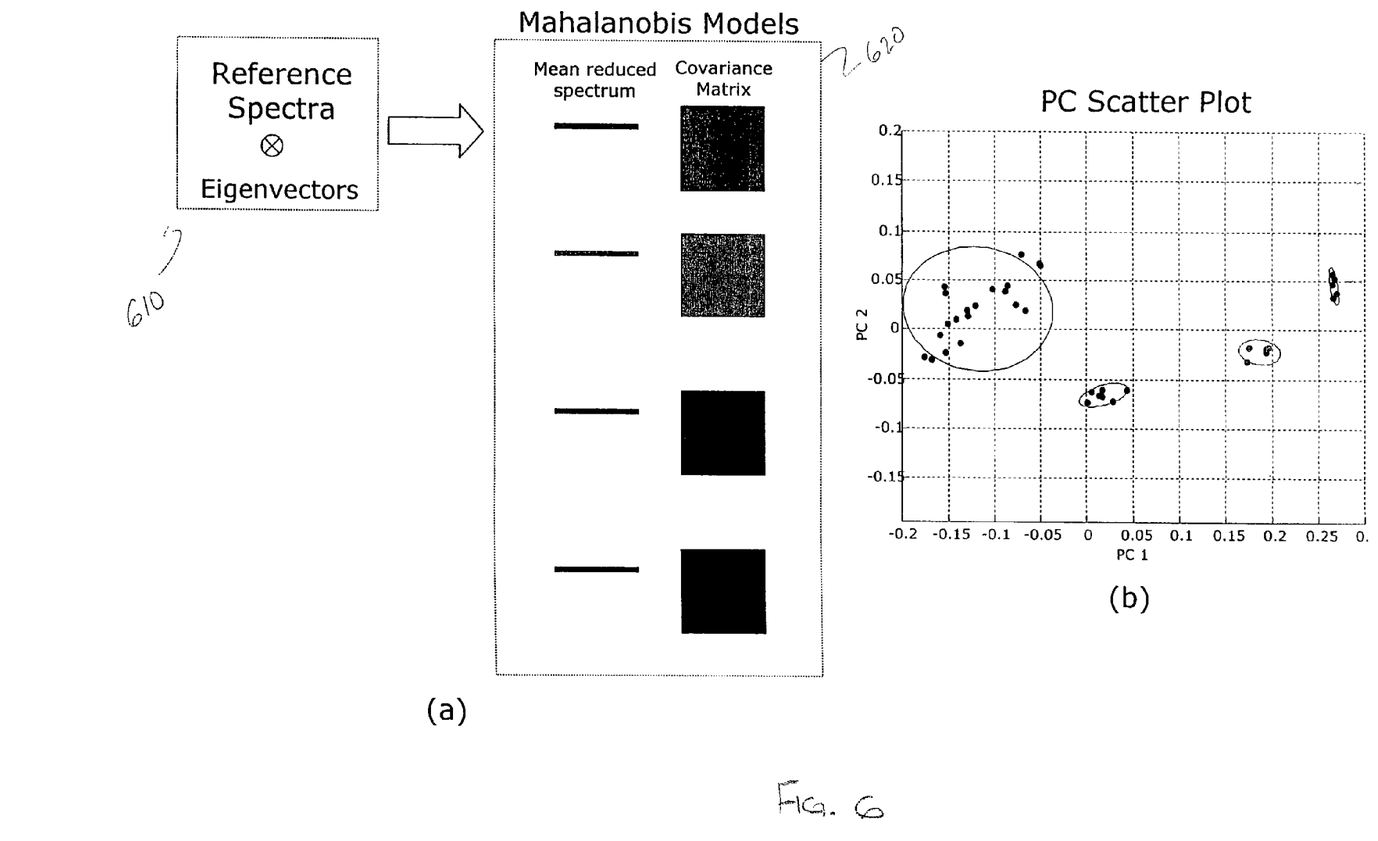
FIG. 6A shows an exemplary method for creating class models from the reference spectra and eigenvectors.
FIG. 6B shows a principal component scatter plot for the model of FIG. 6A.
Figure 7:
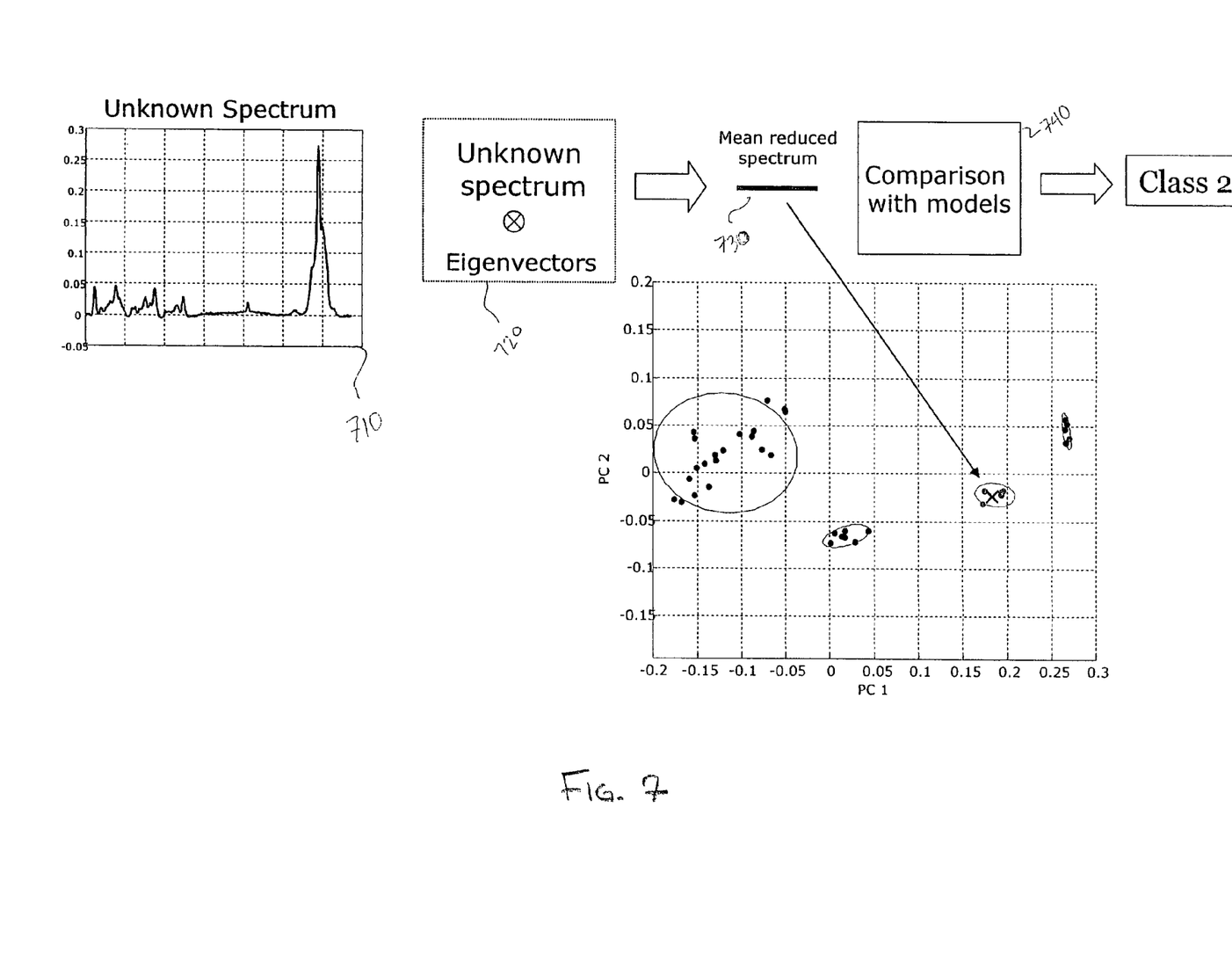
FIG. 7 schematically shows a method for mapping an unknown spectrum to PC space according to one embodiment of the disclosure.

An exemplary application of the method and apparatus according to one embodiment of the disclosure is shown in FIGS. 5-7. Specifically, FIG. 5 shows a method for determining eigenvectors according to one embodiment of the disclosure. Referring to FIG. 5, several reference spectrum are shown as class 1 through class 4. Each class defines a unique spectra which is the fingerprint of the material it represents. Using the principal component analysis, classes 1-4 can be represented as eigenvectors, schematically shown as matrix 540. This information can be stored in the library as discussed in reference to step 110 of FIG. 1.

FIG. 6A shows an exemplary method for creating class models from the reference spectra and eigenvectors. In step 610, the reference spectra are multiplied by the eigenvectors to transform the spectra into a form suitable for inclusion as Mahalanobis models 620.

FIG. 6B shows a principal component scatter plot for the model of FIG. 6A. In the scatter plot each dot represents a spectrum in PC space. Here, principal component 1 (PC1) is plotted on the X-axis, and principal component 2 (PC2) is plotted on the Y-axis. For these classes, PC1 captures the most of the variability among the spectra, as seen by the separation of the classes in the PC1 dimension. The ellipses around the classes represent the 2-σ intervals accounting for approximately 95% of the likelihood of class membership.

FIG. 7 schematically shows a method for mapping an unknown spectrum to PC space according to one embodiment of the disclosure. In FIG. 7, an unknown sample's spectrum is shown as spectrum 710. The unknown spectrum is reduced to eigenvectors in step 720 and a mean reduced spectrum 730 is obtained therefrom. In step 740, the mean reduced spectrum is compared with models existing in the library by mapping the known mean reduced spectrum into PC space. Depending on the location of the known mean reduced spectrum in the PC space and its proximity to the closest known class, the unknown sample can be identified. FIG. 7 illustrates this concept.

While the disclosure has been discussed in reference to specific examples and particular embodiments described herein, it should be noted that the principles disclosed herein are not limited thereto and include variations, modification or departures from those discussed herein.

What is claimed is:

1. A method of assessing the occurrence of an unknown substance in a sample comprising multiple entities, the method comprising:
   providing a reference library comprising a plurality of reference data sets representative of at least one known substance;
   assessing a first feature of the entities wherein the first feature is characteristic of the unknown substance;
   selecting a region of interest of the sample wherein said region of interest comprises at least one entity exhibiting said first feature;
   obtaining a Raman test spectrum from said region of interest;
   performing a first comparison of said Raman test spectrum with said reference data sets using Euclidian distance;
   if said first comparison, results in a match to one of said reference data sets representative of a known substance, identifying said unknown substance as the known substance;
   if said comparing does not result in a match to one of said reference data sets, perform a second comparison of said Raman test spectrum with said reference data sets using Mahalanobis distance; and
   if said second comparison results in a match to one of said reference data sets representative of a known substance, identifying said unknown substance as the known substance.

2. The method of claim 1 wherein said reference data sets of said reference library are obtained using a sensor selected from the group consisting of: an optical imaging sensor, an ultraviolet fluorescence imaging sensor, a Raman dispersive spectroscopy sensor, a Raman imaging sensor, and combinations thereof.

3. The method of claim 1 wherein said reference data sets of said reference library are obtained using a sensor selected from the group consisting of: a near infrared sensor, a mid infrared sensor, and combinations thereof.

4. The method of claim 1 wherein said first feature is assessed using a sensor selected from the group consisting of: an optical imaging sensor, an ultraviolet fluorescence imaging sensor, a Raman dispersive spectroscopy sensor, a Raman imaging sensor, and combinations thereof.

5. The method of claim 1 wherein said first feature is assessed using, a sensor selected from the group consisting of: a near infrared sensor, a mid infrared sensor, and combinations thereof.

6. The method of claim 1 wherein assessing said first feature comprises assessing at least one morphological feature using an optical imaging sensor.

7. The method of claim 6 wherein said at least one morphological feature is selected from the group consisting of: shape, color, diameter, area, perimeter, and combinations thereof.

8. The method of claim 1 wherein spectra from two or more reference data sets are obtained substantially simultaneous from a plurality of sensors.

9. The method of claim 1 wherein said step of selecting a region of interest further comprises selecting one or more target regions within said region of interest wherein said target region comprises at least one entity exhibiting said first feature.

10. The method of claim 1 wherein if said Raman test spectrum has a signal-to-noise ratio below a predetermined threshold, excluding said Raman test spectrum from analysis.

11. The method of claim 1 wherein said method is automated.

12. The method of claim 1 further comprising applying PCA analysis to said reference database to obtain a set of PCA eigenvectors.

13. The method of claim 1 wherein if said comparison results in matching the Raman test spectrum with more than one reference data set, identifying the unknown substance as a mixture.

14. The method of claim 13 further comprising:
   applying a spectral unmixing algorithm to determine at least one of the following: constituents of the mixture, concentration of constituents of the mixture, and combinations thereof.

15. The method of claim 1 wherein if said second comparison does not result in a match to one of said reference data sets representative of a known substance:
   obtaining a spatially accurate wavelength resolved Raman image of said region of interest wherein each pixel of said image is the Raman spectrum for the sample at the corresponding location and assessing said Raman image to thereby identify said unknown substance as a known substance.

16. The method of claim 1 wherein if said second comparison does not result in a match to one of said reference data sets representative of a known substance:
   obtaining a spatially accurate wavelength resolved image of said region of interest wherein each pixel of said image is the Raman spectrum for the sample at the corresponding location; and
   assessing said Raman image to thereby determine at least one of the following: the constitutes of the mixture, the concentration of the constituents of the mixture, and combinations thereof.

17. The method of claim 1 wherein if said second comparison does not result in a match to one of said reference data sets representative of a known substance:
   obtaining a spatially accurate wavelength resolved Raman image of said region of interest wherein each pixel of said image is the Raman spectrum for the sample at the corresponding location;
   assessing said Raman image;
   if said assessing results in identifying said unknown substance as a known substance, reporting said unknown substance as the known substance; and
   if said assessing does not result in identifying said unknown substance as a known substance, performing Ramanomics to determine at least one of the following: presence of proteins in the unknown substance, concentration of proteins in the unknown substance, presence of lipids in the unknown substance, concentration of lipids in the unknown substance, presence of carbohydrates in the unknown substance, concentration of carbohydrates in the unknown substance, and combinations thereof.

18. The method of claim 1 wherein if said second comparison does not result in a match to one of said reference data sets representative of a known substance:
   performing Ramanomics to determine at least one of the following: presence of proteins in the unknown substance, concentration of proteins in the unknown substance, presence of lipids in the unknown substance, concentration of lipids in the unknown substance, presence of carbohydrates in the unknown substance, concentration of carbohydrates in the unknown substance, and combinations thereof.

19. The method of claim 1 wherein said unknown substance is a substance selected from the group consisting of: a chemical substance, a biological substance, a combination of chemical and biological substances, a toxic material, a hazardous material, an inert material, and combinations thereof.

20. The method of claim 1 wherein if said second comparison does not result in a match to one of said reference data sets representative of a known substance, applying a spectral unmixing algorithm to determine at least one of the following: constituents of the mixture, concentration of constituents of the mixture, and combinations thereof.

21. A system for assessing the occurrence of an unknown substance in a sample comprising multiple entities, the system comprising:
   a reference library comprising a plurality of reference data sets representative of at least one known substance;
   a means for assessing a first feature of the entities, wherein the first feature is characteristic of the unknown substance;
   a means for selecting a region of interest of the sample wherein said region of interest comprises at least one entity exhibiting said first feature;
   a means for obtaining a Raman test spectrum from said region of interest;
   a means for performing a first comparison of said Raman test spectrum with said reference data using Euclidian distance;
   a means for performing a second comparison of said Raman test spectrum with said reference data using Mahalanobis distance; and
   a means for identifying said unknown substance as the known substance.

22. The system of claim 21 wherein said reference data sets of said reference library are obtained using a sensor selected from the group consisting of: an optical imaging sensor, an ultraviolet fluorescence imaging sensor, a Raman dispersive spectroscopy sensor, a Raman imaging sensor, and combinations thereof.

23. The system of claim 21 wherein said reference data sets of said reference library are obtained using a sensor selected from the group consisting of: a near infrared sensor, a mid infrared sensor, and combinations thereof.

24. The system of claim 21 wherein said means for assessing said first feature is a sensor selected from the group consisting of: an optical imaging sensor, an ultraviolet fluorescence imaging sensor, a Raman dispersive spectroscopy sensor, a Raman imaging sensor, and combinations thereof.

25. The system of claim 21 wherein said means for assessing said first feature is a sensor selected from the group consisting, of: a near infrared sensor, a mid infrared sensor, and combinations thereof.

26. The system of claim 21 wherein said system is automated.

27. The system of claim 21 further comprising a means for applying PCA analysis to the plurality of reference data sets of the reference library.

28. The system of claim 21 further comprising a means for obtaining a spectrum from two or more reference data sets substantially simultaneously from a plurality of sensors.

* * * * *